(12) United States Patent
Kumar et al.

(10) Patent No.: US 7,470,816 B2
(45) Date of Patent: Dec. 30, 2008

(54) TRAMADOL RECOVERY PROCESS

(75) Inventors: Ashok Kumar, Maharashtra (IN); Suneel Yeshwant Dike, Maharashtra (IN); Satish Rajanikant Soudagar, Maharashtra (IN); Chirag Hasmukh Shah, Maharashtra (IN); Sandeep Madhavrao Burudkar, Maharashtra (IN); Prashant Gautam, Maharashtra (IN); Byju Nellithanath Thankachen, Maharashtra (IN); Ashvini Saxena, Madhya Pradesh (IN); Manavalan Saravanan, Madhya Pradesh (IN); Gunjan Pramod Pathak, Madhya Pradesh (IN); Virendra Pal, Madhya Pradesh (IN); Rahul Karde, Madhya Pradesh (IN); Jaysingh Gehlot, Madhya Pradesh (IN)

(73) Assignee: IPAC Laboratories Limited, Mumbai (IN)

( * ) Notice: Subject to any disclaimer, the term of this patent is extended or adjusted under 35 U.S.C. 154(b) by 49 days.

(21) Appl. No.: 11/598,472

(22) Filed: Nov. 13, 2006

(65) Prior Publication Data

US 2007/0112074 A1    May 17, 2007

(30) Foreign Application Priority Data

Nov. 14, 2005    (IN)    ................ 1422/MUM/2005

(51) Int. Cl.
*C07B 57/00* (2006.01)
*C07C 211/16* (2006.01)

(52) U.S. Cl. ............................ 564/304; 564/455

(58) Field of Classification Search ............... None
See application file for complete search history.

(56) References Cited

U.S. PATENT DOCUMENTS

| 3,652,589 | A | 3/1972 | Flick et al. |
| 5,414,129 | A | 5/1995 | Cherkez et al. |
| 5,672,755 | A | 9/1997 | Lerman et al. |
| 5,723,668 | A | 3/1998 | Buschmann et al. |
| 5,728,885 | A | 3/1998 | Buschmann et al. |
| 5,852,216 | A | 12/1998 | Finkam et al. |
| 5,874,620 | A | 2/1999 | Lerman et al. |
| 5,877,351 | A | 3/1999 | Anderson et al. |
| 6,169,205 | B1 | 1/2001 | Cabri et al. |
| 6,318,650 | B1 | 11/2001 | Breitenbach et al. |
| 6,323,368 | B1 | 11/2001 | Evans |
| 6,399,829 | B1 | 6/2002 | Jarvi et al. |
| 6,469,213 | B1 | 10/2002 | Schickaneder et al. |
| 6,521,792 | B2 | 2/2003 | Akteries et al. |
| 6,649,783 | B2 | 11/2003 | Kupper et al. |
| 6,806,294 | B2 | 10/2004 | Wimmer et al. |
| 6,909,017 | B2 | 6/2005 | Hell |
| 7,030,276 | B2 | 4/2006 | Finkam et al. |
| 2003/0092773 | A1 | 5/2003 | Evans |

FOREIGN PATENT DOCUMENTS

| EP | 0256258 | 2/1988 |
| EP | 0778262 A2 | 6/1997 |
| EP | 0831082 A1 | 3/1998 |
| EP | 0940385 A1 | 9/1999 |
| EP | 1047662 | 11/2000 |
| EP | 1346978 | 9/2003 |
| EP | 1785412 | 5/2007 |
| GB | 997399 | 7/1965 |
| IN | 362/BOM/1996 | 7/1996 |
| WO | WO 99/36389 | 7/1999 |
| WO | WO 99/36390 | 7/1999 |
| WO | WO 99/61405 | 12/1999 |
| WO | WO 02/066414 A1 | 8/2002 |
| WO | WO 03/029186 A1 | 4/2003 |
| WO | WO 03/078380 A2 | 9/2003 |

OTHER PUBLICATIONS

Database CAPLUS on STN, Acc. No. 2002:841080, Bonifacio et al., IT 99MI2023 (Mar. 29, 2001) (abstract).*

* cited by examiner

*Primary Examiner*—Brian J Davis
(74) *Attorney, Agent, or Firm*—Law Offices of Albert Wai-Kit Chan, PLLC

(57) ABSTRACT

A process for the resolution of isomeric tramadol mixtures comprising: providing a purification stock comprising both cis and trans tramadol; contacting the purification stock with an acid under conditions effective to form an acid salt of the cis and trans tramadol in the purification stock; and separating the cis tramadol acid salt from the trans tramadol to obtain a purified cis tramadol acid salt; and optionally converting the cis tramadol acid salt to cis tramadol or to a pharmaceutically active salt thereof.

22 Claims, No Drawings

TRAMADOL RECOVERY PROCESS

FIELD OF INVENTION

The present invention relates to a process for recovery of pure (1R,2R1S,2S)-2-[(dimethylamino)methyl]-1-(3-methoxyphenyl) cyclohexanol i.e., cis-2-[(dimethylamino) methyl]-1-(3-methoxyphenyl)cyclohexanol from a diastereomeric mixture of (cis & trans)-2-[(dimethylamino)methyl]-1-(3-methoxyphenyl) cyclohexanol. The process of the present invention is simple to operate, high yielding and easily scalable to industrial production.

BACKGROUND OF THE INVENTION cis-2-[(Dimethylamino)methyl]-1-(3-methoxyphenyl)cyclohexanol hydrochloride represented below in Formula I, also known as Tramadol hydrochloride under the international non-proprietary name, is considered as a non-addicting analgesic and is useful for the management of moderate or severe pain in human patients.

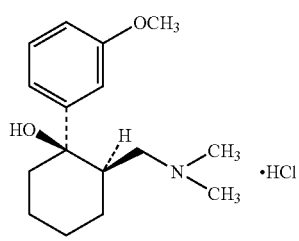

Formula I

The synthesis for tramadol was first disclosed in British patent Nr. 997399, which involves the Grignard reaction of 2-[(dimethylamino)methyl]cyclohexanone with 3-methoxyphenylmagnesium bromide. This reaction yields an isomeric mixture of cis & trans 2-[(dimethylamino) methyl]-1-(3-methoxyphenyl)cyclohexanol. Out of these, the cis-2-[(dimethylamino)methyl]-1-(3-methoxyphenyl) cyclohexanol is the required isomer and its hydrochloride is marketed as tramadol hydrochloride. In the patent synthesis, the isomers were separated by forming a hydrochloride salt of both isomers and selectively isolating the cis-2-[(dimethylamino)methyl]-1-(3-methoxyphenyl)cyclohexanol hydrochloride by crystallizations from 1,4-dioxane.

One disadvantage of this process is that the solvent used for the separation of isomers is 1,4-dioxane which is now considered as an unacceptable toxic material whose tolerability limits are set to an extremely low level. Another disadvantage is that repeated crystallizations were required to get a pharmaceutically acceptable isomeric purity from 1,4-dioxane as a crystallizing solvent. Furthermore 1,4-Dioxane is known to possess industrial safety hazards, as it is susceptible to form hazardous peroxides. Its exposure to workers through skin contact or inhalation poses substantial health risks, as it is a possible carcinogen.

Considerable research has been done in the past to obtain the desired cis-isomer selectively during the Grignard reaction of 2-[(dimethylamino)-methyl]-cyclohexanone with 3-methoxyphenylmagnesium bromide, but, to our knowledge, exclusive cis-isomer formation is unsuccessful. One report, U.S. Pat. No. 7,030,276, claims to get better selectivity of the desired isomer by carrying out the Grignard reaction in the presence of lithium salt, but still the trans-isomer content was reported to be 8%, which is again separated by crystallization from dioxane/water. A further report, W02003029186, describes the use of transition metal complexes of 2-[(dimethylamino)-methyl]-cyclohexanone during the Grignard reaction for enhanced isomer selectivity. The process results in transition metal salts of the (±)-cis/trans tramadol isomeric mixture with a cis/trans ratio of about 85:15 to 98:2, which were protonated with an acid to break the transition metal salts for releasing the cis-tramadol base. The acid protonation is described to facilitate the purification/isolation of cis-tramadol base from the reaction solution comprising the (±)-cis/trans tramadol transition metal salts. It is taught that the protonation procedure will not alter/improve the cis/trans isomer ratio, since the pH is kept sufficiently high to prevent the protonation of the amino group. This current application discloses various organic acid salts of tramadol for pharmaceutical application.

There are several other reports attempting to solve the problem of isolation of pure cis-2-[(dimethylamino)methyl]-1-(3-methoxyphenyl)cyclohexanol from a cis/trans isomeric mixture, since the Grignard reaction invariably yields an isomeric mixture.

One such report, EP Patent No. 0940385, describes separation of cis isomer from the cis/trans mixture by crystallizing cis-tramadol base as a solid from a combination of water & water-miscible organic solvents.

Further reports, WO 99/61405 & WO 99/36390, describe the separation of isomers by forming a hydrochloride, hydrobromide or hydroiodide salt and crystallizing these salts from solvents such as nitriles and alcohols. Repetition of these processes suggests that it is hard to achieve the desired purity of cis-isomer without repeated crystallization and substantial yield losses. The reported results may be achievable on laboratory scale but the process as described would create processing problems if attempted on large scale.

Another report, European Patent No. 831082, describes isomeric separation of a cis/trans mixture by treating the mixture with electrophilic reagents such as thionyl chloride and acetic anhydride, thereby selectively reacting with the hydroxyl group of (1R,2S/1S,2R)-tramadol to give the corresponding derivatives without substantially affecting the cis-isomer and recovering the cis-isomer.

Another modification was published in EP 0778262 that describes isomeric separation of a cis/trans mixture by treating the mixture in acidic conditions using sulphuric acid or para-toluene sulphonic acid, thereby selectively dehydrating the unwanted trans-isomer to the corresponding alkene compound and the cis-isomer is isolated. Also, when the reaction was conducted under aqueous conditions, it was observed that about 50% of the trans-isomer converted to the cis-isomer, thereby achieving a higher cis-isomeric ratio. But the unwanted isomer still remains as a contaminant in the product, which is further purified by forming a hydrochloride salt and crystallizing from a solvent such as isopropyl alcohol.

A similar process was also reported in Indian Patent No.182116, which does not describe any dehydration of the trans-isomer, but conversion of unwanted trans-isomer to cis-isomer by treating with organic/inorganic acid in aqueous system. Both of the above processes operate at high temperatures for said conversion.

Yet another modification, W002066414, describes isomeric separation by forming a salt with saccharin and selectively isolating the cis-2-(dimethylaminomethyl)-1-(3-methoxyphenyl)cyclohexanol as the saccharinate salt and finally converting the salt to tramadol hydrochloride.

Yet another way of recovering the cis-isomer of tramadol from an isomeric mixture is disclosed in WO03078380, which comprises crystallizing the cis-tramadol base as such from the isomeric mixture in the presence of water. This report also describes the isolation of tramadol monohydrate free base by treating the cis&trans isomeric mixture in water and adjusting the pH to 7.5 to 8.5 with an organic acid, and is claimed to improve the trans-isomer content. The process appeared to be not practical for large scale operation since the tramadol base itself is known to exist in an oily form and practically is difficult to crystallize selectively on a large scale.

Another report, U.S. Pat. No. 5,723,668, describes separation of (−)-tramadol and (+)-tramadol using L-(+)-tartaric acid, and isolation of L-(+)-tartrate salt of (−)-2-(dimethylaminomethyl)-1-(3-methoxyphenyl)cyclohexanol, and finally converts it into tramadol. This process leads to four diastereomeric tartrate salts instead of satisfactory separation of the cis/trans isomers, and therefore the corresponding yield is low. To the best of our knowledge there is no report teaching the use of any organic acid for the isomeric separation of tramadol by forming an organic salt except Saccharin and L-(+)-tartaric acid which are expensive chiral separating agents, and which separate both (−) and (+) tramadol. Yet another research in this line is reported in US20030092773 by conventional racemic resolution techniques using chiral tartaric acid derivatives such as O,O-ditoluoyl tartaric acid to resolve the isomers, but these processes also suffer from the problems discussed above and, additionally, the use of chiral organic acids are not economically viable.

Therefore the object of this invention is to develop processes for the recovery of cis-2-(dimethylaminomethyl)-1-(3-methoxyphenyl)cyclohexanol in higher yield without having stringent operation conditions and ensuring better isomeric separation on large scale production.

SUMMARY OF THE INVENTION

According to the present invention there is provided a process for the separation of isomeric tramadol mixtures comprising: providing a purification stock comprising both cis and trans tramadol; contacting the purification stock with an organic acid under conditions effective to form an acid salt of the cis and trans tramadol in the purification stock; and separating the cis tramadol acid salt from the trans tramadol acid salt to obtain a purified cis tramadol acid salt; and optionally converting the cis tramadol acid salt to cis tramadol or to a pharmaceutically active salt thereof.

The organic acid is preferably an achiral one. Preferred acids include benzoic acid, salicylic acid, oxalic acid, phthalic acid, citric acid, para-toluene sulphonic acid, methane sulphonic acid, succinic acid, maleic acid, cinnamic acid and mixtures of two or more thereof. Salicyclic acid and benzoic acids are especially preferred.

The purification stock is preferably contacted with the acid in the presence of a first solvent. The first solvent may be selected from alcohol, water, polar organic solvents, methylene chloride, chloroform, ketonic solvents, ester solvents, hydrocarbons, polar aprotic solvents, ethers; and suitable mixtures of two or more thereof.

Thus, the invention provides a process in accordance with the above for recovery of cis tramadol, i.e. (1R, 2R/1S, 2S)-2-[(dimethylamino) methyl]-1-(3-methoxyphenyl) cyclohexanol of Formula I or its pharmaceutically acceptable salts comprising

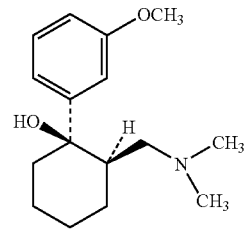

Formula I a) treating a mixture of cis&trans tramadol or a crude reaction mass comprising mainly a mixture of cis&trans tramadol with an organic acid in a first solvent;

b) effecting organic salt formation and recovering selectively said cis-tramadol organic salt substantially free of the trans tramadol salt; and c) converting said organic salt into cis-tramadol hydrochloride As used herein, the phrase "substantially free" means less than about 0.5 percent by weight, preferably less than about 0.25 % by weight, and more preferably less than about 0.1 percent by weight of (±)-trans-tramadol isomer.

The crude reaction mass may be a residue or a solution obtained from the reaction of 2-[(dimethylamino)methyl]-cyclohexanone and 3-methoxyphenyl magnesium bromide or chloride.

The reaction mass containing cis/trans tramadol may be subjected to a pretreatment to remove the inorganic salts.

Separation of the cis-tramadol acid salt may be effected by crystallization, or by extraction followed by crystallization from a second solvent, or by distillation of the first solvent followed by crystallization from a second solvent. In these cases the second crystallizing solvent may be selected from acetone, methanol, ethanol, isoproanol, n-propanol, methylene chloride or their mixtures with water.

Preferably in the above process steps a & b (and also preferably c) are performed in a single pot. The conversion of tramadol organic acid salt into cis-tramadol hydrochloride preferably comprises: treating said organic salt with a base in a solvent; separating the tramadol base from the solution; forming a solution of tramadol base in a crystallizing solvent; and reacting said solution with hydrochloric acid followed by isolating the precipitated cis-tramadol hydrochloride. The first solvent preferably comprises water or water miscible solvents or mixtures thereof.

The crystallizing solvent may be an alcohol or ketone or ethyl acetate, or it may comprise a mixture of water and an organic solvent. In this case, the water is preferably removed azeotropically before crystallizing pure tramadol hydrochloride from the organic solvent.

In the process of the invention the cis-tramadol hydrochloride product is preferably substantially free from trans-isomer. Preferably the trans-tramadol hydrochloride content in the product is less than 0.1% by weight Also provided in accordance with the invention are pharmaceutical compounds comprising cis-tramadol in substantially pure form free from trans-tramadol. Preferably, the cis tramadol present in such compositions is recovered in substantially pure form by means of the process of the invention before being incorporated into a pharmaceutical product.

DETAILED DESCRIPTION OF INVENTION

Accordingly a method for recovery of pure cis-2-(dimethylaminomethyl)-1-(3-methoxyphenyl)cyclohexanol isomer from a cis/trans mixture of ratio varying from a range of 40:60 to 98:2 in high yield and high isomeric purity using organic acids is developed in the present invention.

According to the present invention, the process includes the steps of: converting the free tramadol base or an impure tramadol base directly obtained from the Grignard reaction of 2-[(dimethylamino)methyl]-1-cyclohexanone with 3-methoxyphenyl magnesium halide, into an organic acid salt in a first solvent and recovering such salt from the first solvent by conventional methods like distillation, precipitation etc.; selectively crystallizing the pure cis-2-(dimethylaminomethyl)-1-(3-methoxyphenyl)cyclohexanol organic acid salt from a second solvent selected from alcohols, ketones, ethers, nitrites or their combination with water or a combination of polar and non polar solvent like methylene chloride, hexane etc.; and finally converting the said salt of pure cis-2-(dimethylaminomethyl)-1-(3-methoxyphenyl)cyclohexanol into tramadol or its pharmaceutically acceptable salts (for example hydrochloride).

The invention will now be described in detail in connection with certain preferred and optional embodiments, so that various aspects thereof may be more fully understood and appreciated.

This invention provides an industrial purification method for tramadol substantially free from its unwanted trans-isomer, which method ameliorates problems associated with achieving isomeric purity of tramadol, and provides reproducibly high yields.

In one aspect of the present invention, a process is provided for recovery of cis-2-(dimethylaminomethyl)-1-(3-methoxyphenyl)cyclohexanol (cis-tramadol) from its isomeric impurity, trans-2-(dimethylaminomethyl)-1-(3-methoxyphenyl)cyclohexanol. The process comprises converting the isomeric mixture of 2-(dimethylaminomethyl)-1-(3-methoxyphenyl)cyclohexanol free base into an organic acid salt in a first solvent; eliminating the first solvent to recover organic acid salt of cis/trans 2-(dimethylaminomethyl)-1-(3-methoxyphenyl) cyclohexanol mixture; selectively precipitating the cis isomer of 2-(dimethylaminomethyl)-1-(3-methoxyphenyl) cyclohexanol organic acid salt from a second solvent(s) characterized by alcoholic solvent, ketonic solvents or ethers or nitrites or their mixture with water while the trans-isomer remain in solution; separating the precipitated cis-2-(dimethylaminomethyl)-1-(3-methoxyphenyl)cyclohexanol organic acid salt; and converting the recovered salt into Tramadol hydrochloride.

In the process according to the invention, the starting isomeric tramadol base may be free from other impurities, or the tramadol base obtained directly from the reaction of 2-(dimethylaminomethyl)-cyclohexanone with 3-methoxyphenyl bromide of varying cis/trans isomeric ratio without added purification may be used. The cis/trans isomeric ratio can be as high as 40:60 to 98:2 in the starting tramadol base, but preferably it is about 83:17 ratio since the isomeric ratio of the mass obtained after Grignard coupling is about 83:17.

In the process, the isomeric mixture of tramadol base is treated with about 0.5 to 2 mole equivalents of the organic acid, preferably stoichiometric quantities of organic acid. The organic acid found to be particularly suitable for isomeric separation are, although not limited to, benzoic acid, salicylic acid, oxalic acid, phthalic acid, citric acid, para-toluene sulphonic acid, methane sulphonic acid, succinic acid, maleic acid, and cinnamic acid. Preferably the acid is benzoic acid or salicylic acid.

The salt formation can be carried out at a temperature range of 0-50° C., but preferably the salt is formed at room temperature or with adequate cooling to avoid any undue exotherm. The solvents useful for the salt formation are any organic solvent, a mixture of organic solvents, water, or a mixture of organic solvent & water. Preferably the isomeric salts were isolated from the salt forming solvent by conventional means such as filtration, centrifugation, distillation or the like. Preferably the solvent is eliminated by distillation to form the organic acid salt and then the solvent is changed to a second crystallization solvent. The crystallization solvents are selected from alcohols, ketones, ethers, nitriles or their combination with water, mixture of polar and non-polar organic solvents such as methylene chloride-hexane, preferably a combination of water and water miscible solvents are used. The amount of solvent may be determined based on the nature of solvent(s) or solvent combinations or their solubility patterns. For the most part, although not always, 2 to 10 parts by volume of solvent relative to the mass of cis/trans tramadol organic acid salt is found to be ideal for isomeric separation. In the process the organic acid salt of cis/trans tramadol in the crystallization solvent is heated to reflux until completely dissolved, optionally filtered to remove any insoluble mass, cooled to precipitate the cis tramadol organic acid salt selectively while the trans-isomer remains in solution. The solution at reflux is preferably first cooled to room temperature and kept for a holding period at room temperature before chilling to about 0° C. The precipitated cis-2-[(dimethylamino)methyl]-1-(3-methoxyphenyl)-cyclohexanol organic acid salt is isolated by conventional means like filtration, centrifugation etc. and optionally dried at room temperature or higher temperature at atmospheric or reduced pressures. Preferably the wet product is taken for further conversion to tramadol hydrochloride.

Finally the organic acid salt of pure cis-2-[(dimethylamino) methyl]-1-(3-methoxyphenyl) cyclohexanol is basified by conventional methods and converted to pure tramadol hydrochloride.

The following examples, which include preferred embodiments, will serve to illustrate the practice of this invention, it being understood that the particulars shown are by way of example and for purpose of illustrative discussion of preferred embodiments of the invention.

EXAMPLE

Example 1

Tramadol benzoate

In a reaction flask 24.1 g tramadol base (of cis/trans ratio about 83:17) was mixed with 100 ml methylene chloride. 11.50 gm of benzoic acid was added into the mixture and stirred for about 2 hours. The solvent was then removed by evaporation under reduced pressure. The residue obtained was mixed with 110 ml methanol and water in ratio of 95:5. The mass was heated to reflux for 1 hour and cooled to room temperature and maintained for additional 1 hour. Further the mass was chilled to 10° C., precipitated salt was filtered, washed with methanol and dried under vacuum to obtain 22.4 gm (63%) cis-2-[(dimethylamino) methyl]-1-(3-methoxyphenyl)cyclohexanol benzoate salt (cis =99.62% & trans =0.38%).

Example 2

Tramadol salicylate

In a reaction flask 65.25 g tramadol base (of cis/trans ratio about 83:17) was mixed with 100 ml methylene chloride. 34.26 gm of salicylic acid was added into the mixture and stirred for about 2 hours. The solvent was then removed by evaporation under reduced pressure. The residue obtained was mixed with 115 ml methanol: water in ratio of 95:5. The mass was heated to reflux for 1 hour and cooled to room temperature and maintained for additional 1 hour. Further the mass was chilled to 10° C., precipitated salt was filtered, washed with methanol and dried under vacuum to obtain 70.95 gm (71%) cis-2-[(dimethylamino) methyl]-1-(3-methoxyphenyl)-1-cyclohexanol salicylate salt (cis =99.1 & trans =0.88).

Example 3

Tramadol salicylate

In a reaction flask 168.3 g tramadol base (of cis/trans ratio about 83:17) was mixed with 547.2 ml methanol-water mixture 487.5 ml (methanol:water ratio—3:0.23 v/v) and 86.59 gm of salicylic acid was added and stirred for about 30 minutes. The mass was heated to reflux for 30 minutes and cooled to room temperature & maintained for further 30 minutes. The mass was then chilled to 5 degrees, the precipitated salt was filtered, washed with chilled methanol and dried under vacuum to obtain 158.52 gm (69.32%) cis-2- [(dimethylamino) methyl]-1-(3-methoxyphenyl)-1-cyclohexanol salicylate salt (cis=99.98 & trans=0.02 by HPLC area %).

Example 4

Tramadol hydrochloride

In a reaction flask 29 g tramadol salicylate salt was stirred with 87 ml water and pH was adjusted to 11-12 by 10% aqueous KOH solution. The tramadol free base was extracted with methylene chloride, organic extract washed with water, and methylene chloride was evaporated under reduced pressure. The oil obtained was dissolved in 88.0 ml methylene chloride. Stirred and cooled to 15° C. Adjusted pH to 2-2.5 by conc. HCl. Stirred for 1.0 hour at same temperature. Raised the temperature to 25-30° C. and stirred it for 30 minutes. Distilled out solvent completely under vacuum. Charged 42 ml acetone and stirred at 25-30° C. for 30 minutes. Filtered the product and washed solid with acetone. Yield=18.4 gm (85%) (cis=99.98% & trans=0.02% by HPLC area%).

Example 5

Tramadol hydrochloride

In a reaction flask 22g tramadol benzoate salt was stirred with 66ml water and pH was adjusted to 11-12 by 10% aqueous KOH solution. The tramadol free base was extracted with methylene chloride, organic extract washed with water, and methylene chloride was evaporated under reduced pressure. The oil obtained was dissolved in 76 ml methylene chloride. Stirred and cooled to 15° C. Adjusted pH to 2-2.5 by conc. HCl. Stirred for 1.0 hour at same temperature. Raised the temperature to 25-30° C. and further stirred for 30 mns. Distilled out solvent completely under vacuum. Charged 36 ml acetone and stirred at 25-30° C. for 30 mins. Filtered the product and washed the solid with acetone.

Yield=15.6 gm (91%) (cis=99.98% & trans=0.02% by HPLC area%).

Example 6

Tramadol hydrochloride.

In a reaction flask 200 g tramadol salicylate salt was stirred with 1 liter water and pH was adjusted to 11-12 by 30% aqueous NaOH solution. The tramadol free base was extracted with toluene, washed with water, and toluene was evaporated under reduced pressure. The oil obtained was dissolved in 650 ml isopropyl alcohol. The pH of solution was adjusted to 2-3 by conc. HCl (about 33 ml). 500 ml hexane was added to the above solution and water was removed by distillation. After complete removal of water, the solvent was completely evaporated. The residue was mixed with 1.5 liter acetone and stirred at 25-27° C. for 30 minutes. The precipitated product was filtered, washed with cold acetone and dried to give 140 gm (93.65%) Tramadol hydrochloride (cis=99.98% & trans=0.02%).

Example 7

Tramadol hydrochloride

In a reaction flask 160 g tramadol salicylate (or benzoate) salt was stirred with about 800 ml water and pH was adjusted to 11-12 by 30% aqueous NaOH solution. The tramadol free base was extracted with toluene, washed with water, and toluene was evaporated under reduced pressure. The oil obtained (about 100 gm) was dissolved in 300 ml isopropyl alcohol. In a separate flask HCl gas was passed in isopropyl alcohol. This isopropyl alcohol-HCl solution was added to tramadol base solution in isopropyl alcohol at about 30° C. till the pH attained 3-4. The mixture was stirred, heated to about 75° C., and then cooled to 0-5° C. The precipitated product was filtered, washed with chilled isopropyl alcohol and dried to obtain 92 gm Tramadol hydrochloride (cis=99.95% & trans=0.05%).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

The invention claimed is:

1. A process for purifying cis-tramadol (1R,R2/1S,2S)-2-[(dimethylamino)methyl]-1-(3-methoxyphenyl)cyclohexanol from an isomeric tramadol mixtures, comprising the steps of:
   providing a purification stock comprising both cis- and trans-tramadol;
   contacting the purification stock with an organic acid under conditions effective to form an acid salt of the cis- and trans-tramadol in the purification stock;
   precipitating cis-tramadol acid salt from the purification stock and leaving trans tramadol in the purification stock; and optionally converting the cis-tramadol acid salt to cis-tramadol or to a pharmaceutically active salt thereof.

2. A process according to claim 1 wherein the organic acid is achiral.

3. A process according to claim 1 wherein the organic acid is selected from benzoic acid, salicylic acid, oxalic acid, phthalic acid, citric acid, para-toluene sulphonic acid, methane sulphonic acid, succinic acid, maleic acid, cinnamic acid and mixtures of two or more thereof.

4. A process according to claim 3 wherein the acid is selected from salicylic acid and benzoic acid.

5. A process according to claim 1, wherein the purification stock is contacted with the acid in the presence of a first solvent.

6. A process according to claim 5 wherein the first solvent is selected from alcohol, water, polar organic solvents, methylene chloride, chloroform, ketonic solvents, ester solvents, hydrocarbons polar aprotic solvents ethers;
and suitable mixtures of two or more thereof.

7. A process according to claim 1 for recovery of cis tramadol (1R,2R/1S,2S)-2-[(dimethylamino) methyl]-1-(3-methoxyphenyl) cyclohexanol (Formula I) or its pharmaceutically acceptable salts comprising

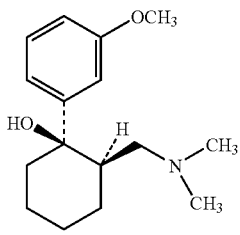

Formula I a) combining a mixture of cis & trans-tramadol or a crude reaction mass comprising a mixture of cis & trans tramadol with an organic acid in a first solvent;
b) effectuating organic salt formation and crystallizing said cis-tramadol organic salt substantially free of the trans-tramadol salt; and
c) converting said organic salt into cis-tramadol or a pharmaceutically acceptable salt.

8. A process according to claim 7, wherein the crude reaction mass is a residue or a solution obtained from the reaction of 2-[(dimethylamino)methyl]cyclohexanone and 3-methoxyphenyl magnesium bromide or chloride.

9. A process according to claim 8, wherein the reaction mass containing cis/trans-tramadol is subjected to a pretreatment to remove the inorganic salts.

10. A process according to claim 7, wherein crystallizing of the cis-tramadol acid salt is effected by crystallization from the first solvent.

11. The process according to claim 10, wherein the first solvent is acetone, methanol, ethanol, isopropanol, n-propanol, methylene chloride or their mixtures with water.

12. A process according to claim 7, wherein crystallizing of the cis-tramadol acid salt is effected by extraction followed by crystallization from a second solvent.

13. A process according to claim 7, wherein crystallizing of the cis-tramadol acid salt is effected by distillation of the first solvent followed by crystallization from a second solvent.

14. A process according to claim 12 wherein the second crystallizing solvent is selected from acetone, methanol, ethanol, isopropanol, n-propanol, methylene chloride or their mixtures with water.

15. A process according to claim 13 wherein the second crystallizing solvent is selected from acetone, methanol, ethanol, isopropanol, n-propanol, methylene chloride or their mixtures with water.

16. A process according to claim 7, wherein the step a & b are performed in a single pot.

17. A process according to claim 1 wherein the conversion of tramadol organic acid salt into cis-tramadol hydrochloride comprises
a) treating said organic salt with a base in a solvent;
b) separating the tramadol base from the solution;
c) forming a solution of tramadol base in a crystallizing solvent; and
d. reacting said solution with hydrochloric acid followed by isolating the precipitated cis-tramadol hydrochloride.

18. A process according to claim 17, wherein the crystallizing solvent is an alcohol or ketone or ethyl acetate.

19. A process according to claim 17, wherein the crystallizing solvent is a mixture of water and an organic solvent.

20. A process according to claim 17 wherein the cis-tramadol hydrochloride is substantially free from trans-isomer.

21. A process according to claim 20, wherein the trans-tramadol hydrochloride is less than 0.1%.

22. A process according to claim 7, wherein the pharmaceutically acceptable salt of cis-tramadol is hydrochloride salt.

* * * * *

UNITED STATES PATENT AND TRADEMARK OFFICE
CERTIFICATE OF CORRECTION

PATENT NO. : 7,470,816 B2
APPLICATION NO. : 11/598472
DATED : December 30, 2008
INVENTOR(S) : Ashok Kumar et al.

It is certified that error appears in the above-identified patent and that said Letters Patent is hereby corrected as shown below:

Title page, item (73) Assignee section, "IPAC Laboratories Limited, Mumbai (IN)" should be --IPCA Laboratories Limited, Mumbai (IN)--

Title page, item (57) ABSTRACT section, "and separating the cis tramadol acid salt from the trans tramadol to obtain a purified cis tramadol acid salt; and optionally converting the cis tramadol acid salt to cis tramadol or to a pharmaceutically active salt thereof" should be --and separating the cis-tramadol acid salt from the trans-tramadol to obtain a purified cis-tramadol acid salt; and optionally converting the cis-tramadol acid salt to cis-tramadol or to a pharmaceutically active salt thereof--

In column 3, line 3, "cisitrans" should be --cis/trans--

In column 3, line 44, "trans tramadol" should be --trans-tramadol--

In column 3, line 45, "cis tramadol acid salt from the trans tramadol" should be --cis-tramadol acid salt from the trans-tramadol--

In column 3, line 46, "cis tramadol" should be --cis-tramadol--

In column 3, line 47, "converting the cis tramadol acid salt to cis tramadol" should be --converting the cis-tramadol acid salt to cis-tramadol--

In column 3, line 64, "cis tramadol" should be --cis-tramadol--

In column 4, line 19-20, "trans tramadol salt" should be --trans-tramadol salt--

In column 4, lines 66-67, "cis tramadol" should be --cis-tramadol--

In column 6, line 28, "cis tramadol" should be --cis-tramadol--

In column 8, lines 56-58, "1. A process for purifying cis-tramadol (1R,R2/1S,2S)-2-[(dimethylamino)methyl]-1-(3-methoxyphenyl)cyclonexanol from an isomeric tramadol" should be --1. A process for purifying cis-tramadol, (1R,2R/1S,2S)-2-[(dimethylamino)methyl]-1-(3-methoxyphenyl)cyclohexanol, from an isomeric tramadol--

UNITED STATES PATENT AND TRADEMARK OFFICE
CERTIFICATE OF CORRECTION

PATENT NO. : 7,470,816 B2
APPLICATION NO. : 11/598472
DATED : December 30, 2008
INVENTOR(S) : Ashok Kumar et al.

It is certified that error appears in the above-identified patent and that said Letters Patent is hereby corrected as shown below:

In column 9, lines 20-22, "A process according to claim 1 for recovery of cis tramadol (1R,2R/1S,2S)-2-[(dimethylamino)methyl]-1-(3-methoxyphenyl) cyclohexanol (formula I)" should be --A process according to claim 1 for the recovery of cis-tramadol, (1R,2R/1S,2S)-2-[(dimethylamino)methyl]-1-(3-methoxyphenyl) cyclohexanol, (formula I)--

Signed and Sealed this

Twenty-fourth Day of February, 2009

JOHN DOLL
*Acting Director of the United States Patent and Trademark Office*